United States Patent
Gari et al.

(10) Patent No.: US 9,539,231 B2
(45) Date of Patent: Jan. 10, 2017

(54) METHOD FOR TREATING TRIPLE-NEGATIVE BREAST CANCER USING AMPI-109

(71) Applicants: The Regents of the University of Colorado, a body corporate, Denver, CO (US); Trustees of Boston University, Boston, MA (US)

(72) Inventors: Hamid Gari, Aurora, CO (US); Jim Lambert, Aurora, CO (US); Scott Lucia, Aurora, CO (US); Rahul Ray, Boston, MA (US); Ann Thor, Aurora, CO (US)

(73) Assignees: The Regents of the University of Colorado, a body corporate, Denver, CO (US); Trustees of Boston University, Boston, MA (US)

( * ) Notice: Subject to any disclaimer, the term of this patent is extended or adjusted under 35 U.S.C. 154(b) by 0 days.

(21) Appl. No.: 14/158,238

(22) Filed: Jan. 17, 2014

(65) Prior Publication Data
US 2015/0202173 A1  Jul. 23, 2015

(51) Int. Cl.
*A61K 31/215* (2006.01)
*A61K 31/337* (2006.01)
*A61K 31/704* (2006.01)

(52) U.S. Cl.
CPC ........... *A61K 31/215* (2013.01); *A61K 31/337* (2013.01); *A61K 31/704* (2013.01)

(58) Field of Classification Search
None
See application file for complete search history.

(56) References Cited

U.S. PATENT DOCUMENTS

| 2003/0129194 | A1 | 7/2003 | Mazess et al. |
| 2005/0059641 | A1* | 3/2005 | Ray et al. ............ 514/167 |
| 2005/0142162 | A1 | 6/2005 | Hunter et al. |
| 2010/0292231 | A1 | 11/2010 | Ajami et al. |
| 2010/0304989 | A1 | 12/2010 | Von Hoff et al. |
| 2011/0237556 | A1 | 9/2011 | DeLuca et al. |
| 2013/0072389 | A1 | 3/2013 | Penny et al. |

FOREIGN PATENT DOCUMENTS

| EP | 1687041 | 8/2006 |
| EP | 2494077 | 9/2012 |
| WO | 2005/027926 | 3/2005 |
| WO | 2011/119622 | 9/2011 |

OTHER PUBLICATIONS

Lopes N, et al., "1Alpha,25-dihydroxyvitamin D3 Induces de novo E-cadherin Expression in Ttriple-Negative Breast Cancer Cells by CDH1-Promoter Demethylation", Publication Types, MeSH Terms, Substances, Anticancer Res. Jan. 2012:32(1): 249-57.
"Implementation and Refinement of High Throughput Functional Genomic Screening", Progress Report—Oct. 2012.
Song Yao, "Pretreatment Serum Concentrations of 25-Hydroxyvitamin D and Breast Cancer Prognostic Characteristics: A Case-Control and a Case-Series Study", Feb. 28, 2011.
"Lambert Lab", Pathology, University of Colorado Denver, Feb. 6, 2013.

* cited by examiner

*Primary Examiner* — Layla Bland
(74) *Attorney, Agent, or Firm* — Don D. Cha; Hamilton DeSanctis & Cha, LLP (57) ABSTRACT

A targeted approach toward the treatment of TN breast cancer by using AMPI-109 is disclosed. AMPI-109 is a compound with remarkable "cancer-specific" characteristics. In particular, AMPI-109 demonstrates a striking targeted capability to inhibit the proliferation of TN breast cancer cells and to induce apoptosis in TN breast cancer cells. The growth inhibitory effect of AMPI-109 is independent of VDR. AMPI-109 can also be coupled with other oncolytic agents in treating a patient with TN breast cancer.

5 Claims, 7 Drawing Sheets

METHOD FOR TREATING TRIPLE-NEGATIVE BREAST CANCER USING AMPI-109

This application was prepared with financial support from the Saudi Arabian Cultural Mission (SACM).

BACKGROUND

Field of the Invention

The present invention relates to the use of 1α,25-Dihydroxyvitamin $D_3$-3β-bromoacetate (AMPI-109) for treatment of triple negative (TN, also called basal-like (BL)) breast cancer.

Description of the Related Art

Breast cancer is a heterogeneous disease exhibiting diverse biological characteristics and clinical responses. Gene expression profiling has defined genetic signatures corresponding to at least five distinct molecular subtypes of breast cancer including an aggressive form known as TN breast cancer.

There are three molecules that have been identified to promote many breast cancers: estrogen receptor (ER), progesterone receptor (PR), and human epidermal growth factor receptor 2 (HER2). By definition, TN breast cancer fails to express these three molecules. Although TN breast cancer represents a relatively small percentage of all breast cancers (~20%), it is typically high grade (poorly differentiated) and rapidly progressive, with a higher risk of relapse and lower survival than other subtypes of breast cancer. Therefore, TN breast cancer is associated with a disproportionate number of deaths. Additionally, for unknown reasons, TN breast cancer is often diagnosed in younger women and women of African-American descent.

Current clinical approaches for breast cancer typically include agents that target the three molecules identified to promote many breast cancers, such as endocrine therapies and the monoclonal antibody trastuzumab targeting HER2. Because TN breast cancer is defined as absence of these targets, conventional cytotoxic chemotherapy is currently the mainstay systemic treatment for patients with TN breast cancer. However, conventional systemic treatments are limited by poor therapeutic response, high toxicity, and the development of resistance. Although new approaches in the treatment of TN breast cancer such as targeting DNA repair with PARP inhibitors have emerged, there have been relatively fewer therapeutic advances in TN breast cancer when compared to other subtypes of the disease. Thus, there is a pressing need for targeted approaches toward the treatment of TN breast cancer.

In view of these problems, an object of the present invention is to develop an effective method for treating TN breast cancer. Another object is to develop a method targeting TN breast cancer cells of various molecular subtypes with little or no effect on normal cells. These and other objects have been achieved according to the present invention.

SUMMARY

One aspect of the present invention is directed to a method of treating TN breast cancer by administering an effective amount of AMPI-109 to a patient.

Another aspect is directed to a method of treating TN breast cancer using combination therapy. The administration of the components can be carried out simultaneously or in tandem.

In another aspect, AMPI-109 is administered with doxorubicin.

In another aspect, AMPI-109 is administered with paclitaxel.

In another aspect, AMPI-109 is administered with both doxorubicin and paclitaxel.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Throughout this description all ranges described include all values and sub-ranges therein, unless otherwise specified. Additionally, the indefinite article "a" or "an" carries the meaning of "one or more" throughout the description, unless otherwise specified.

After conducting a wide scale study and evaluations of various compounds which may function as an effective targeted treatment for TN breast cancer, the inventors have surprisingly discovered that AMPI-109 has the characteristic of killing TN breast cancer cells of various molecular subtypes and that AMPI-109 has no effect on untransformed cells, which suggests a critical "cancer-specific" mode of this compound's action. The inventors have found that AMPI-109 promotes apoptotic death of TN breast cancer cells through alterations of MAPK signaling and that AMPI-109 exerts its potent pro-apoptotic actions through a novel mode of action.

AMPI-109, which has a chemical structure as shown below, is a vitamin D (1,25D) analog, with a bromoacetate substitution at position three of the A ring:

It has the property of covalently binding to the ligand binding domain. AMPI-109 was initially developed as a biochemical tool to identify the residues of the ligand binding domain of the nuclear vitamin D receptor (VDR) that contact the hormone (U.S. Patent Application Publication No. US 2005/0059641 to Ray et al., the entire teaching of which is incorporate herein by reference). Vitamin D and most other vitamin D analogs exert their antitumorigenic properties largely through binding to VDR. Surprisingly, AMPI-109 behaves differently. The inventors have found that VDR is not required for the antitumorigenic properties of AMPI-109. Indeed, AMPI-109 exerts its growth inhibitory effects through pathway(s) separate from those of vitamin D action. Because of AMPI-109's distinct mechanism of action, AMPI-109 would be a promising candidate as an effective therapeutic agent in treating TN breast cancer, and possibly other cancer types such as leukemia.

Breast cancer is a very heterogeneous disease consisting of multiple molecular subtypes. In order to examine the antitumorigenic properties of AMPI-109 in human breast cancer cells of various subtypes, a cohort of breast cancer cell lines were treated with AMPI-109 at its $IC_{50}$ (the dose where 50% of the cells show the desired effects), equimolar 1,25D or ethanol control and cellular growth was quantified. In particular, the cell lines were treated at the approximate $IC_{50}$ (100 nM) of AMPI-109, 1,25D (100 nM) or ethanol control for 3 days. MTS assays were then performed. The experiment was repeated three times with 6 replicates per experiment. The representative data were summarized in Table 1.

TABLE 1

| Cell Line | Subtype* | 1,25D % Control | AMPI-109 % Control | 1,25D: AMPI-109 p-value |
|---|---|---|---|---|
| MCF10A | Nonmalignant | 102 | 99 | 0.23 |
| MCF7 | Luminal A | 95 | 93 | 0.27 |
| T47D | Luminal A | 98 | 94 | 0.40 |
| BT-474 | Luminal B | 87 | 66 | <0.0001 |
| MDA-453 | HER2 | 94 | 86 | 0.26 |
| SKBR3 | HER2 | 100 | 99 | 0.89 |
| MDA-231 | TN (MSL) | 96 | 44 | <0.0001 |
| MDA-468 | TN (BL1) | 86 | 39 | <0.0001 |
| BT-20 | TN (Unclass.) | 82 | 29 | <0.0001 |
| BT-549 | TN (M) | 94 | 69 | <0.0001 |
| HCC70 | TN (BL2) | 83 | 49 | <0.0001 |
| SUM149 | TN (BL2) | 92 | 39 | <0.0001 |

*TN: triple negative; MSL: mesenchymal stem like; BL1: basal like 1; Unclass.: unclassified; M: mesenchymal; BL2: basal like 2.

The percentage in Table 1 represents growth compared to control treatment. The p values represent significance of difference between 1,25D inhibition and AMPI-109 inhibition of growth. It can be concluded from the data that AMPI-109 inhibits the growth of multiple TN breast cancer subtypes and this inhibition appeared to be almost entirely specific for TN breast cancer cell lines. Indeed, AMPI-109 appears to be specific for cancer cells in general and does not inhibit the growth of non-malignant breast (MCF10A) or luminal A subtypes (MCF7, T47D).

Figure 1:
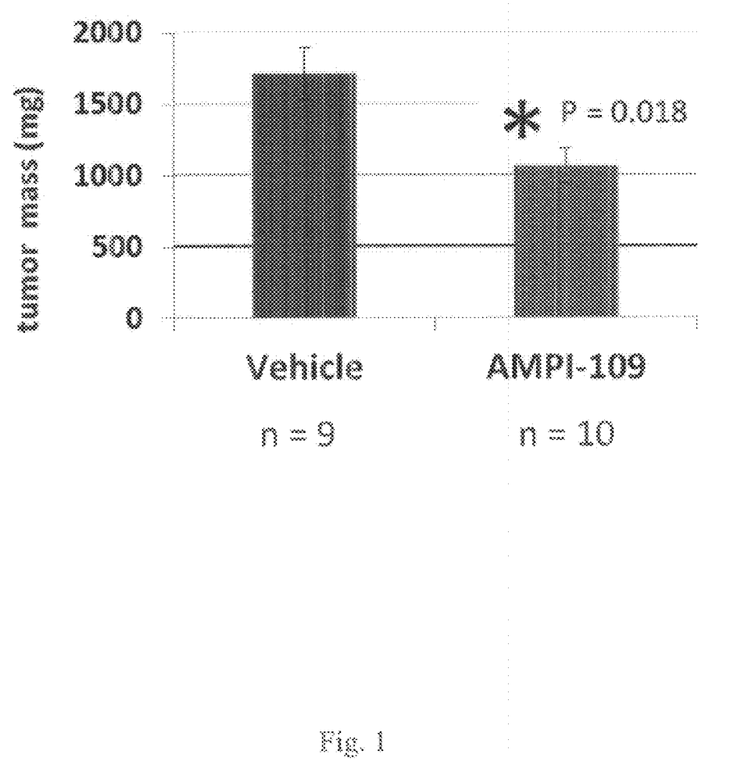
FIG. 1 shows the effect of AMPI-109 on the growth inhibition of a human TNBC tumor xenograft.

The inventors further examined the ability of AMPI-109 to inhibit the growth of a patient-derived triple negative breast cancer tumor xenograft. A tumor from a woman diagnosed with stage 4 triple negative breast cancer was propagated by serial passage through NOD-SCID mice. The tumor was dissected into equal sizes and implanted into the left and right mammary fat pads of 12 NOD-SCID mice. Once the tumors reached 100 mm³ in size the mice were randomized into vehicle- and AMPI-109-treated arms. A total of 19 tumors grew out (9 for vehicle, and 10 for AMPI-109 treated). Vehicle control or AMPI-109 (1 ug/kg body weight) was administered by i.p. injection every other day for three weeks. Upon completion of the study, the tumors were excised and volume and mass were determined. A significant reduction in both volume and mass was observed in mice treated with AMPI-109. The results were shown in FIG. 1, where * indicates a p value of 0.018, which was determined by T-test. As shown in FIG. 1, AMPI-109 reduced the size of the tumors by approximately 30%.

Figure 2A:
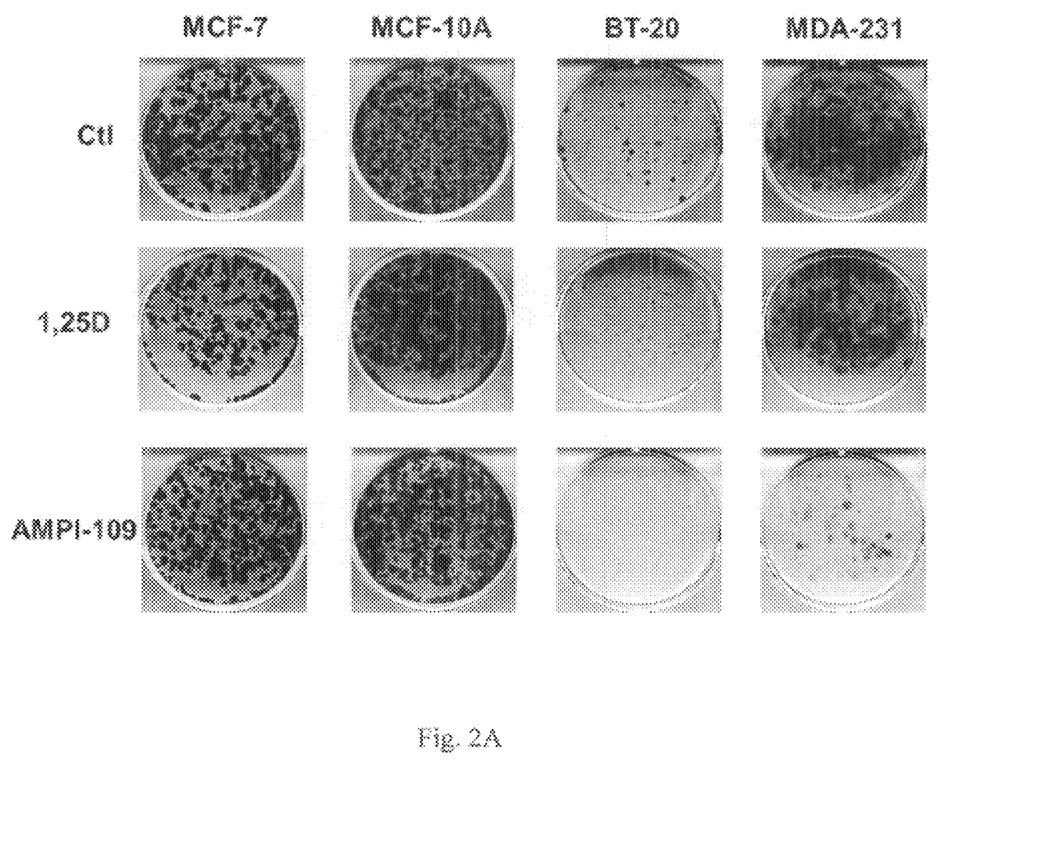
FIG. 2A shows the selective effect of AMPI-109 on TNBC cell viability as measured by crystal violet staining assays.

In order to determine the effects of AMPI-109 on cell viability as one possible explanation of the reduction in tumor size, the inventors plated various breast cancer cell lines in 6-well dishes and treated with either ethanol control (CU), vitamin D (1,25D) or AMPI-109. 1,25D and AMPI-109 were administered at 100 nM. The plates were incubated for 7 days and cell viability was assessed by crystal violet staining. As shown in FIG. 2A, a significant reduction in cell viability was observed in AMPI-109 treated TNBC cell lines (BT-20, MDA-231), whereas AMPI-109 had no effect on cell viability of non-malignant (MCF-10A) or luminal A (MCF7) subtype breast cancer cell lines.

Figure 2B:
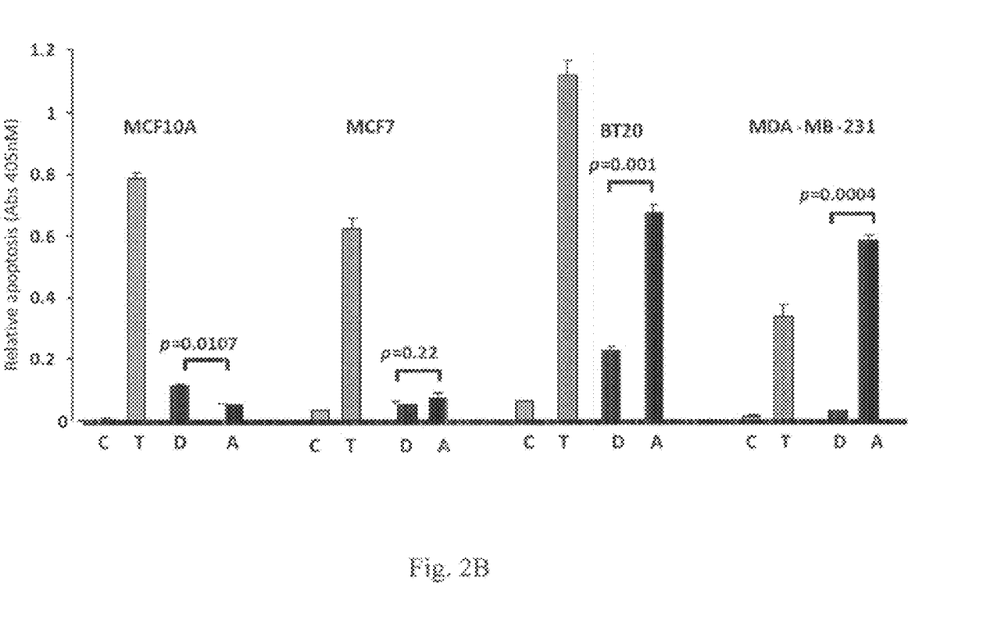
FIG. 2B shows the effect of AMPI-109 induced apoptosis as measured by ELISA assays for various cell lines treated with different agents.

The inventors also examined the ability of AMPI-109 to induce apoptosis in TN breast cancer cells by performing ELISA assays. Various cell lines (MCF10A, MCF-7, BT-20 and MDA-231) were treated with ethanol control (C), paclitaxel (100 nM, (T)), 1,25D (100 nM), (D)), or AMPI-109 (100 nM), (A)) for 24 hours. ELISA assays were then performed. The results were summarized in FIG. 2B. The p values in the figure were determined by T-test. FIG. 2B shows a strong induction of apoptosis in the TN breast cancer cell lines MDA-231 and BT-20, but not in the non-TN breast cancer cell lines MCF-7 or MCF-10A, following treatment with AMPI-109. In contrast, paclitaxel, a commonly used drug in treating breast cancer, induced apoptosis in all cells tested. Therefore, it can be concluded that AMPI-109 appears to specifically induce apoptosis in TN breast cancer cells.

Figure 2C:
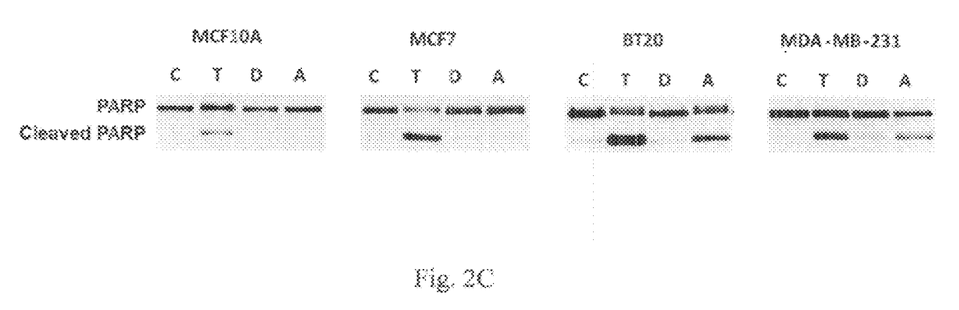
FIG. 2C shows PARP cleavage determined by western blot for various cell lines treated with different agents.

Cleavage of poly (ADP)-ribose polymerase (PARP), a hallmark of apoptosis, was used to further investigate the ability of AMPI-109 to induce apoptosis of TN breast cancer cells. FIG. 2C, wherein PARP cleavage was determined by western blot, summarizes the results of cleaved PARP after treating MCF10A, MCF-7, BT-20 and MDA-231 with ethanol control (C), paclitaxel (100 nM, (T)), 1,25D (100 nM), (D)), or AMPI-109 (100 nM, (A)) for 24 hours. The studies showed that AMPI-109 promoted PARP cleavage only in BT-20 and MDA-231 cells. Accordingly, the results as described in FIG. 2A, FIG. 2B, and FIG. 2C indicate the capability of AMPI-109 as an agent to induce apoptosis of TN breast cancer cells.

Typically, 1,25D analog acts on cells through binding to the VDR. Because AMPI-109 is an analog of 1,25D, presumably, AMPI-109, like other 1,25D analogs, exerts its antitumorigenic properties through binding to VDR. Surprisingly, after conducting extensive examinations of the role of VDR in AMPI-109 action and comparing the action of AMPI-109 to the action of other 1,25D analogs, the inventors have found that AMPI-109 acts independently of the VDR and AMPI-109 acts by a novel mechanism distinct from other 1,25D analogs.

Figure 3A:
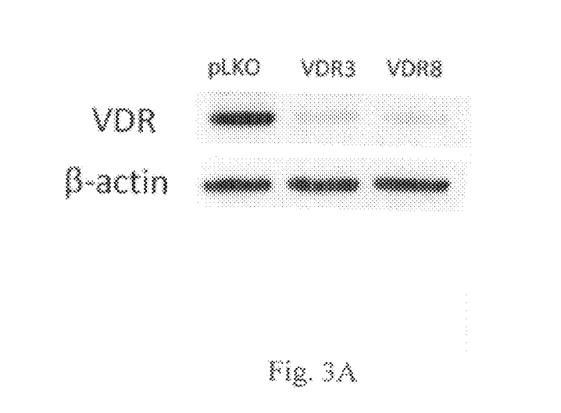
FIG. 3A shows the results of immunoblot analysis of VDR in two pools of BT-20 cells with VDR shRNAs.
Figure 3B:
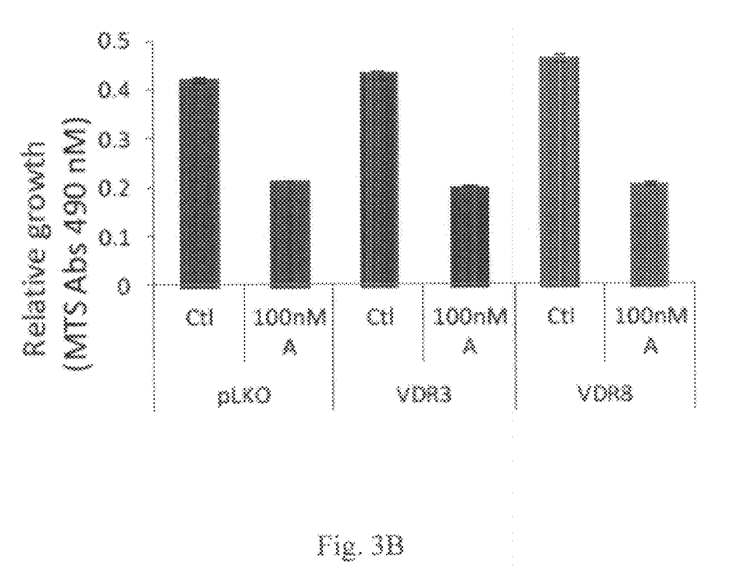
FIG. 3B shows the results of growth assays after treatment with AMPI-109 (A) for 72 hours.

The inventors used shRNAs directed against VDR in BT-20 cells and examined the response after treatment with AMPI-109. In particular, cellular proliferation assays following treatment with AMPI-109 were performed on cells exhibiting knock down of VDR. FIG. 3A shows the immunoblot analysis results of VDR in two pools of BT-20 cells with VDR shRNAs (VDR3 and VDR8). The non-silencing control is designated as pLKO. FIG. 3B shows the results of growth assays following treatment with AMPI-109 for 72 hours. As shown in FIG. 3B, AMPI-109 was equally effective at inhibiting the growth of control cells ($p<0.001$) and cells with VDR knocked down ($p<0.001$). These results thus demonstrate that AMPI-109 mediates its antitumorigenic activities in TN breast cancer cells through a non-VDR-dependent mechanism, thus distinguishing its unique clinical potential from other 1,25D analogs.

VDR activates gene expression as a heterodimer with the retinoid X receptor (RXR). The inventors thus also tested whether pharmacologic inhibition of the VDR axis with HX531, an RXR antagonist, would block AMPI-109-mediated growth inhibition of BT-20 cells. The inventors found that at doses which blocked VDR-mediated gene expression, HX531 did not inhibit the antiproliferative effects of AMPI-109.

The above results indicate that, despite their related chemical structures, AMPI-109 elicits its unique pro-apoptotic actions in TN breast cancer cells through a mechanism distinct from other 1,25D analogs.

Because AMPI-109 demonstrates a remarkable targeted capability to inhibit the proliferation of TN breast cancer cells and to induce apoptosis in TN breast cancer cells and its growth inhibitory effect is independent of VDR, AMPI-109 would be a promising candidate as an effective target therapeutic agent in treating TN breast cancer, and possibly other cancer types such as leukemia.

It is known that chemotherapeutic approaches toward combating cancer are often hampered by resistance and toxicity. Combinatorial drug treatments are thus often employed to overcome these issues. AMPI-109 synergizes with other therapeutic agents, such as paclitaxel and doxorubicin, in inhibition of TN breast cancer cells.

Figure 4:
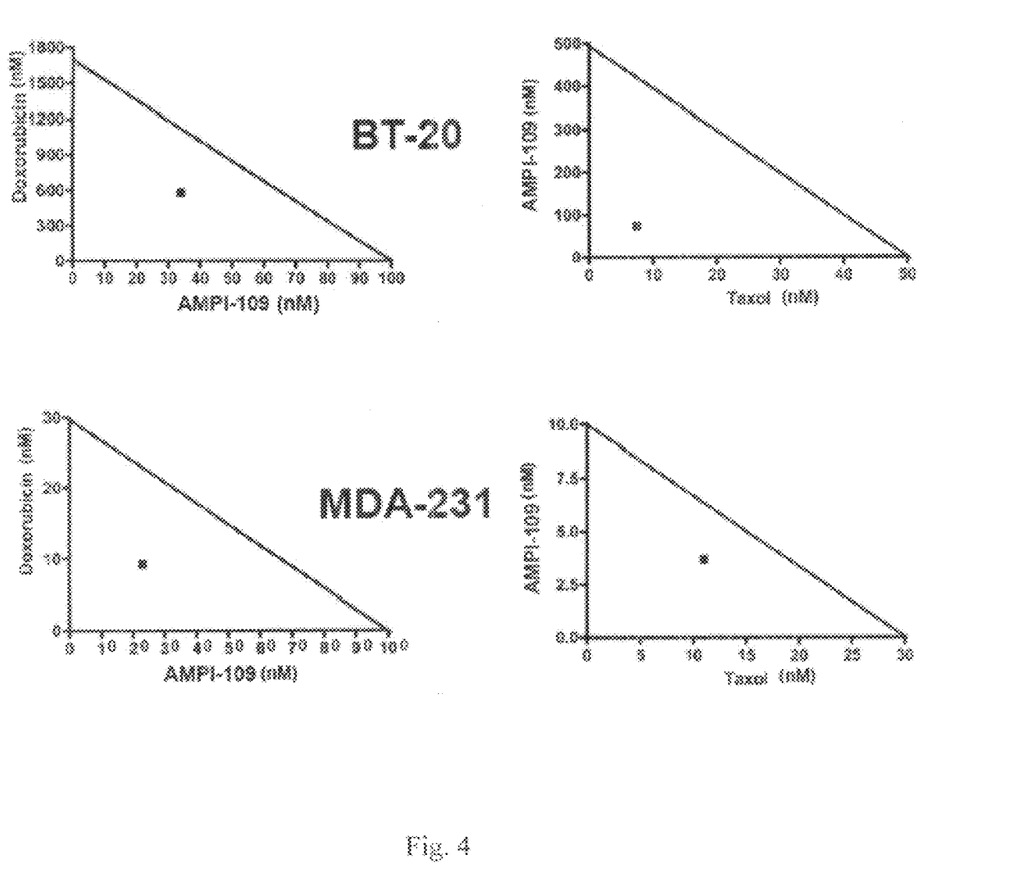
FIG. 4 shows the synergy of AMPI-109 with doxorubicin and paclitaxel in growth inhibition of BT-20 and MDA-231 cells.

Paclitaxel and doxorubicin are the two drugs commonly used in clinic to treat breast cancer. The inventors investigated the synergistic effects on the inhibition of cell viability using AMPI-109 in combination with doxorubicin or paclitaxel by isobolographic analysis. The exemplary results directed to BT-20 and MDA-231 cells were summarized in FIG. 4. Isobolograms were constructed by first determining the $IC_{50}$ values for AMPI-109, doxorubicin and paclitaxel using the MTS cell viability assay. The ratio of these values was used to establish the molar ratio of AMPI-109, doxorubicin and paclitaxel subsequently used. BT-20 and MDA-231 cells were treated with these combinations at increasing concentrations and a new concentration-dependent curve was plotted. Isobolograms were constructed by plotting the experimentally determined $IC_{50}$ values for AMPI-109, doxorubicin and paclitaxel when administered alone, on the X- and Y-axes. In the figure, the diagonal line connecting these values represents the theoretical additive line of these two compounds. The experimental $IC_{50}$ values of AMPI-109 with either doxorubicin or paclitaxel, when coadministered, were graphed on the isobologram. The results of these analyses showed that the determined $IC_{50}$ values, which are represented by the points in the figure, were significantly below the additive line, which indicates a strong synergistic interaction of these compounds.

One embodiment of the present invention is directed to a method of treating TN breast cancer by administering an effective amount of AMPI-109 to a patient. An "effective amount" is an amount of an agent required to achieve a predetermined physiological effect, such as tumor size reduction, while not exceeding the patient's tolerance for the agent. It is understood that an effective amount can vary depending upon the mode of administration, and severity of the condition being treated, as well as the various physical factors related to the individual being treated. The variables include the specific condition and its state as well as the size, age and response pattern of the patient.

For example, a daily dosage of AMPI-109 can be between about 0.01 µg to about 50 µg. A preferred daily dosage can range from 0.05 to 25 µg. A more preferred daily dosage may range from about 0.1 to 10 µg.

A compound comprising an effective amount of AMPI-109 can be given in daily dose or episodic dose, for example, once every 2-6 days or once every two weeks, the dose in each day can be a single dose or divided into several subdoses which can be given, for example, 2-3 hours apart until the total dose is given.

Another embodiment of the present invention is directed to the treatment of TN breast cancer by using combination therapy. A patient is administered a combination of an effective amount of AMPI-109 and at least one of the other known oncolytic agents, such as paclitaxel and doxorubicin. The administration of the components can be carried out simultaneously or in tandem.

The combination may include antitumor drugs such as cycle-active agents and non-cycle-active agents. Cycle-active agents are drugs that require a cell to be in cycle, i.e., actively going through the cell cycle preparatory to cell division to be cytotoxic. Some of these drugs are effective primarily against cells in one of the phases of the cell. The importance of this designation is that cell cycle-active agents are usually schedule-dependent, and that duration of exposure is as important as and usually more important than dose. In contrast, non-cycle-active agents are usually not schedule-dependent, and effects depend on the total dose administered, regardless of the schedule. Alkylating agents are generally considered to be non-cycle-active, whereas antimetabolites are prototypes of cycle-active compounds.

An example of cell cycle-active agents is fluoropyrimidines, such as 5-fluorouracil (5-FU) and 5-fluorodeoxyuridine (5-FUdR). 5-FU and 5-FUdR have antitumor activity against several solid tumors, most notably colon cancer, breast cancer, and head and neck cancer.

Cytosine arabinoside (ara-C) is an antimetabolite analog of deoxycytidine and is the drug of choice for the treatment of acute myelocytic leukemia. In the analog, the OH group is in the β configuration at the 2' position. Ara-C is converted intracellularly to the nucleotide of triphosphate (ara-CTP)

that is both an inhibitor of DNA polymerase and incorporated into DNA. The latter event is considered to cause the lethal action of ara-C.

There is a myriad of other chemotherapeutics considered to be within the scope of the present invention. For example, epipodophyllotoxin, which is a derivative of podophyllotoxin that is used in the treatment of cancers such as leukemia and Hodgkin's, and antibiotics, such as anthracyclines, doxorubicin, daunorubicin, and mitoxantrone, which have antitumor activity.

Paclitaxel, in the present invention, should be understood to include prodrugs, analogues and derivatives thereof, such as TAXOL®, TAXOTERE®, Docetaxel, 10-desacetyl analogues of paclitaxel and 3'N-desbenzoyl-3'N-t-butoxy carbonyl analogues of paclitaxel. Representative examples of such paclitaxel derivatives or analogues include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium 1,2-benzenedicarboxylate, 10-desacetoxy-11,12-dihydrotaxol-10,12(18)-dien-e derivatives, 10-desacetoxytaxol, Protaxol (2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotal, 10-desacetoxy-7-deoxy-9-deoxotaxol, derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'γ-aminobutyryltaxol formate, 2'-acetyl taxol, 7-acetyl taxol, 7-glycine carbamate taxol, 2'-OH-7-P EG(5000) carbamate taxol, 2'-benzoyl and 2',7-dibenzoyl taxol derivatives, other prodrugs (2'-acetyltaxol; 2',7-diacetyltaxol; 2'succinyltaxol; 2'-(beta-alanyl)-taxol); 2'γ-amino-butyryl-taxol formate; ethylene glycol derivatives of 2'-succinyl-taxol; 2'-glutaryltaxol; 2'-(N,N-dimethylglycyl) taxol; 2'-(2-(N,N-dimethylamino)propionyl)taxol; 2'orthocarboxybenzoyl taxol; 2'aliphatic carboxylic acid derivatives of taxol, Prodrugs {2'(N,N-diethylamino-propionyl)taxol, 2'(N,N-dimethyglycyl)taxol, 7(N,N-dimethyl-glycyl)taxol, 2',7-di-(N,N-dimethylglycyl)taxol, 7(N,N-diethylaminopropionyl)taxol, 2',7-di(N,N-diethyl-aminopropionyl)taxol, 2'-(L-glycyl)taxol, 7-(L-glycyl)taxol, 2',7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl) taxol, 2',7-di(L-leucyl)taxol, 2'-(L-isoleucyl)taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl) taxol, 7-(L-phenylalany) taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl) taxol, 7-(L-glutamyl)taxol, 2',7-di(L-glutamyl)taxol, 2'-(L-arginyl)taxol, 7-(L-arginyl)taxol, 2',7-di(L-arginyl)taxol}, Taxol analogs with modified phenylisoserine side chains, taxotere, (N-debenzoyl-N-tert-(butoxycaronyl-)-10-de-acetyltaxol, and taxanes (e.g., baccatin III, cephalomannine, 10-deacetylbaccatin III, brevifoliol, yunantaxusin and taxusin).

Doxorubicin, in the present invention, should be understood to include prodrugs, analogues and derivatives thereof, including differentially hydroxylated versions of daunorubicin which are used for the management of cancer.

Pharmaceutical compositions suitable for use in the present invention include compositions wherein the active ingredients are contained in a therapeutically effective amount to achieve its intended purpose. A therapeutically effective amount means an amount effective to prevent development of or alleviate the existing symptoms and underlying pathology of the subject being treated. Determination of the therapeutically effective amount is well within the capability of those skilled in the art.

It is appreciated that the actual preferred amount of each active component in a specific case will vary according to the efficacy of the specific component employed, the particular compositions formulated, the mode of application, and the particular situs and organism being treated. For example, the specific dose for a particular patient depends on age, sex, body weight, general state of health, diet, the timing and mode of administration, the rate of excretion, and medicaments used in combination and the severity of the disorder. Dosages for a given host can be determined using conventional considerations, e.g., by customary comparison of the differential activities of the subject compounds and of a known agent, such as by means of an appropriate conventional pharmacological protocol. The effective amount of each active component in the combination may be lower than the effective amount of each active component when it is administered alone.

The pharmaceutical compositions for use in accordance with the present invention can be manufactured in a manner that is known, for example, by means of conventional mixing, dissolving, granulating, levigating, emulsifying, encapsulating, entrapping or lyophilizing processes. In addition, the pharmaceutical compositions can be formulated in conventional manner using one or more physiologically acceptable carriers comprising excipients and auxiliaries, which facilitate processing of the active compounds into preparations that can be used pharmaceutically. Proper formulation is dependent upon the route of administration chosen.

The active components identified in the present invention can be administered to a patient by itself or in pharmaceutical compositions where it is mixed with suitable carriers or excipients at an effective amount. Techniques for formulation and administration of the compounds of the instant invention are well within the capability of those skilled in the art.

Suitable routes of administration in the present invention include oral, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the composition in a local rather than systemic manner, such as via injection of the composition directly into an affected area, often in a depot or sustained release formulation.

Furthermore, one can administer the composition in a targeted drug delivery system, such as in a liposome coated with an antibody specific for affected cells. The liposomes will be targeted to and taken up selectively by the cells.

The amount of the administered composition administered dependents on the subject being treated and on the subject's weight, the severity of the affliction, the manner of administration and the judgment of the prescribing physician.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinyl-pyrrolidone (PVP). If desired, disintegrating agents can be added, such as the cross-linked polyvinyl pyrrolidone, agar, or alginic acid or a salt thereof such as sodium alginate.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

For injection, the agents of the invention can be formulated in aqueous solutions, preferably in physiologically compatible buffers such as Hank's solution, Ringer's solution, or physiological saline buffer. For transmucosal administration, penetrants appropriate to the barriers to be permeated are used in the formulation. Such penetrants are generally known in the art.

The compositions can be formulated for parenteral administration by injection, e.g., by bolus injection or continuous infusion. Formulations for injection can be presented in unit dosage for, e.g., in ampoules or in multidose containers, with added preservatives. The compositions can take such forms as suspensions, solutions or emulsions in oily or aqueous vehicles, and can contain formulatory agents such as suspending, stabilizing and/or dispersing agents.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

What is claimed is:

1. A method for treating triple-negative breast cancer, comprising:
    administering a drug comprising AMPI-109 in an amount effective for treating or preventing triple-negative breast cancer to a patient in need thereof, wherein AMPI-109 has a chemical structure of 2. The method of claim 1, wherein the drug further comprises an oncolytic agent in an effective amount.

3. The method of claim 2, wherein the oncolytic agent is at least one selected from the group consisting of doxorubicin and paclitaxel.

4. The method of claim 2, wherein the oncolytic agent is doxorubicin.

5. The method of claim 2, wherein the oncolytic agent is paclitaxel.

* * * * *